United States Patent [19]

Walter et al.

[11] Patent Number: 4,524,203

[45] Date of Patent: Jun. 18, 1985

[54] 4-(4-PYRIDINYL)ISATOIC ANHYDRIDE

[75] Inventors: Thomas J. Walter; Paul F. Ranken, both of Baton Rouge, La.

[73] Assignee: Ethyl Corporation, Richmond, Va.

[21] Appl. No.: 523,462

[22] Filed: Aug. 15, 1983

[51] Int. Cl.$^3$ .................. C07D 265/26; C07D 215/20
[52] U.S. Cl. .................................... 544/94; 546/156; 546/161
[58] Field of Search .................. 546/161, 156; 544/94

[56] References Cited

U.S. PATENT DOCUMENTS 3,838,156  9/1974  Brundage .................. 260/295.5 R

OTHER PUBLICATIONS

Hardtmann et al., J. of Heterocyclic Chem., vol. 12, 1975.

Primary Examiner—Donald G. Daus
Assistant Examiner—Cecilia Shen
Attorney, Agent, or Firm—Donald L. Johnson; John F. Sieberth; Patricia J. Hogan

[57] ABSTRACT 4-(4-Pyridinyl)isatoic anhydrides are prepared by reacting a 2-amino-4-(4-pyridinyl)benzoic acid, i.e., an acid, ester, or salt, with phosgene, preferably gaseous phosgene. The products are particularly useful in the preparation of antibacterial 1-alkyl-1,4-dihydro-4-oxo-7-pyridinyl-3-quinolinecarboxylic acids.

2 Claims, No Drawings

4-(4-PYRIDINYL)ISATOIC ANHYDRIDE

FIELD OF THE INVENTION

This invention relates to 4-(4-pyridinyl)isatoic anhydrides, a process for preparing them, and processes for preparing derivatives thereof.

BACKGROUND

As disclosed in Sterling Drug's U.S. Pat. Nos. 3,753,993 (Lesher et al.), 3,907,808 (Lesher and Carabateas), and 4,118,557 (Lesher), it is known that antibacterial 1-alkyl-1,4-dihydro-4-oxo-7-pyridinyl-3-quinolinecarboxylic acids can be prepared from 4-(3-aminophenyl)pyridine. It is also known that this route to the bactericides, as disclosed, is less economical than might be desired.

From Mitscher et al., "Quinoline Antimicrobial Agents. 1. Versatile New Synthesis of 1-Alkyl-1,4-dihydro-4-oxo-3-quinolinecarboxylic Acids," *Journal of Medicinal Chemistry*, 1978, Vol. 21, No. 5, pp. 485–489, it is also known that antimicrobial agents related to the aforementioned bactericides can be prepared from the appropriate isatoic anhydrides.

It would be desirable to be able to prepare the antibacterial agents of Lesher, Lesher et al, and Lesher and Carabateas by a route similar to that employed by Mitscher et al; and 4-(4-alkyl-3-nitrophenyl)pyridines, as well as 2-nitro- and 2-amino-4-(4-pyridinyl)benzoic acids, that are useful in this regard are disclosed in (1) copending application Ser. No. 511,887, filed July 8, 1983, in the name of Thomas J. Walter (Walter), (2) copending application Ser. No. 511,854, filed July 8, 1983, in the name of V. Ramachandran (Ramachandran), and (3) copending application Ser. No. 511,844, filed July 8, 1983, in the names of Paul F. Ranken and Thomas J. Walter (Ranken and Walter).

*Organic Syntheses*, Collective Volume 3, pages 488–490, teaches that isatoic anhydrides can be prepared by treating an aqueous solution of the hydrochloride salt of an anthranilic acid with gaseous phosgene.

SUMMARY OF INVENTION

An object of this invention is to provide 4-(4-pyridinyl)isatoic anhydrides which are convertible to 1-alkyl-1,4-dihydro-4-oxo-7-pyridinyl-3-quinolinecarboxylic acids.

Another object is to provide a process for preparing the 4-(4-pyridinyl)isatoic anhydrides.

A further object is to provide a process for preparing derivatives of the 4-(4-pyridinyl)isatoic anhydrides.

These and other objects are attained by reacting a 2-amino-4-(4-pyridinyl)benzoic acid with phosgene to form a 4-(4-pyridinyl)isatoic anhydride and, when appropriate, converting the anhydride to a desired derivative thereof.

DETAILED DESCRIPTION

2-Amino-4-(4-pyridinyl)benzoic acids utilizable in the practice of the invention are compounds corresponding to the formula:

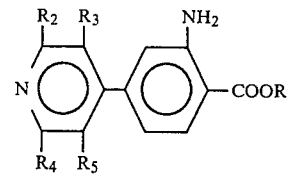

wherein R is hydrogen, an alkali metal, or an alkyl group containing 1–6 carbons and $R_2$, $R_3$, $R_4$, and $R_5$ are independently selected from hydrogen and innocuous substituents, such as substituted (e.g., halogenated) and unsubstituted aryl or aryloxyaryl groups, halo, etc.

Since these compounds are preferably prepared by the process of Ranken and Walter, the teachings of which are incorporated herein by reference, they are generally synthesized by oxidizing a 4-(4-alkyl-3-nitrophenyl)pyridine to a 2-nitro-4-(4-pyridinyl)benzoic acid, salt, or ester and reducing the product to the corresponding amino compound. However, they may also be prepared by the process of Ramachandran, the teachings of which are also incorporated herein by reference—i.e., by treating a 4-(4-alkyl-3-nitrophenyl)pyridine with an alcoholic base to form a 2-amino-4-(4-pyridinyl)benzoic acid, salt, or ester. In any case, the 2-amino-4-(4-pyridinyl)benzoic acid employed may be a pure compound or the crude reaction product obtained by the particular synthesis employed. As indicated in Ranken and Walter and in Ramachandran, the preferred 2-amino-4-(4-pyridinyl)benzoic acid, when the aforementioned bactericides are to be prepared, is 2-amino-4-(4-pyridinyl)benzoic acid itself or a salt or ester thereof.

In the process of the invention, the 2-amino-4-(4-pyridinyl)benzoic acid is reacted with phosgene to prepare the 4-(4-pyridinyl)isatoic anhydride. This reaction may be accomplished, e.g., by treating the hydrochloride salt of the 2-amino-4-(4-pyridinyl)benzoic acid with liquid phosgene or by treating a slurry of the 2-amino-4-(4-pyridinyl)benzoic acid in 1N HCl with liquid phosgene. However, it is preferably effected by treating a dilute basic solution of the 2-amino-4-(4-pyridinyl)benzoic acid with gaseous phosgene. The latter technique produces the desired product as a solid which is readily isolated by filtration of the crude reaction mixture.

The 4-(4-pyridinyl)isatoic anhydrides formed in the process of the invention are novel compounds corresponding to the formula:

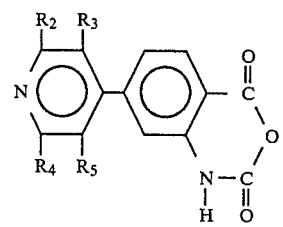

wherein $R_2$, $R_3$, $R_4$, and $R_5$ have the same definitions as given above. When the aforementioned bactericides are to be prepared, the preferred product is 4-(4-pyridinyl)isatoic anhydride itself. These compounds are useful in the synthesis of a variety of materials but are particularly useful as intermediates in the production of the antibacterial 1-alkyl-1,4-dihydro-4-oxo-7-pyridinyl-3-quinolinecarboxylic acids of Lesher, Lesher et al., and Lesher and Carabateas, i.e., compounds corresponding to the formula:

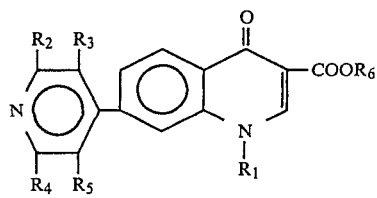

wherein $R_6$ is hydrogen or alkyl, $R_1$ is alkyl, haloalkyl, or hydroxyalkyl, and $R_2$, $R_3$, $R_4$, and $R_5$ have the same definitions as given above—any aliphatic groups generally containing 1–6 carbons.

The synthesis of these bactericides from the 4-(4-pyridinyl)isatoic anhydrides may be accomplished by:

(1) N-alkylating the anhydrides by reaction with a suitable alkylating agent, e.g., the appropriate organic halide (an alkyl halide, vinyloxyalkyl halide, or the like) and—when necessary—treating the product to form the desired N-alkyl, N-hydroxyalkyl, or N-haloalkyl group, as in copending application Ser. No. 522,792, filed Aug. 15, 1983, in the names of Paul F. Ranken and Thomas J. Walter (Ranken et al.), the teachings of which are incorporated herein by reference, (2) reacting the resultant N-alkyl-4-(4-pyridinyl)isatoic anhydride—generally an N-ethyl compound—with an alkali metal salt of an alkyl (e.g., ethyl) formyl acetate, as in Mitscher et al., to form an alkyl 1-alkyl-1,4-dihydro-4-oxo-7-pyridinyl-3-quinolinecarboxylate, e.g., ethyl 1-ethyl-1,4-dihydro-4-oxo-7-pyridinyl-3-quinolinecarboxylate, and (3) hydrolyzing the alkyl 1-alkyl-1,4-dihydro-4-oxo-7-pyridinyl-3-quinolinecarboxylate to the corresponding 1-alkyl-1,4-dihydro-4-oxo-7-pyridinyl-3-quinolinecarboxylic acid.

The following example is given to illustrate the invention and is not intended as a limitation thereof.

EXAMPLE

Part A

A solution of 4 g of 87% pure 2-nitro-4-(4-pyridinyl)benzoic acid in 31 ml of water and 17 ml of 1N potassium hydroxide was shaken overnight in a suitable reaction vessel with 0.4 g of 5% palladium-on-carbon at 40 psi of hydrogen. The pressure dropped to 36 psi, and the catalyst was removed by filtration and washed three times with 15 ml of water. A 10 ml portion of the filtrate was acidified to a pH of 6.5 with 1N HCl to give 0.63 g of yellow crystals having infra-red and nm spectra consistent with 2-amino-4-(4-pyridinyl)benzoic acid. Recrystallization of the hydrochloride salt of the 2-amino-4-(4-pyridinyl)benzoic acid from water gave bright yellow crystals having a melting point of 280°–281° C.

Part B

The remaining 37 ml of filtrate were combined with the filter cake wash and treated with phosgene gas for 20 minutes. The yellow solution deposited tan solids which redissolved and reprecipitated as additional phosgene was added. The solids were collected by filtration and dried to give 2.5 g of tan solids. The tan solids were reslurried in 15 ml of water, the pH adjusted to 7.5 with 1N potassium carbonate, and the product dried to give 2.2 g of 4-(4-pyridinyl)isatoic anhydride as a bright yellow solid. Recrystallization of the product from N,N-dimethylformamide provided bright yellow crystals having a melting point of 265°–267° C.

It was found that the 4-(4-pyridinyl)isatoic anhydride prepared in the preceding examples could be converted to 1-ethyl-1,4-dihydro-4-oxo-7-pyridinyl-3-quinolinecarboxylic acid by (a) alkylating it with ethyl bromide, as in Ranken et al., to produce N-ethyl-4-(4-pyridinyl)isatoic anhydride, (b) reacting the N-ethyl-4-(4-pyridinyl)isatoic anhydride with the potassium salt of ethyl formyl acetate to form ethyl 1-ethyl-1,4-dihydro-4-oxo-7-pyridinyl-3-quinolinecarboxylate, and (c) hydrolyzing that ester.

It is obvious that many variations may be made in the products and processes set forth above without departing from the spirit and scope of this invention.

We claim:

1. A 4-(4-pyridinyl)isatoic anhydride corresponding to the formula:

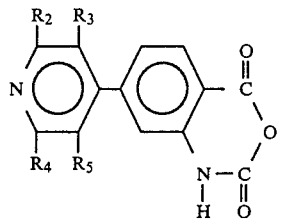

wherein $R_2$, $R_3$, $R_4$, and $R_5$ are independently selected from hydrogen and phenyl, phenoxy phenyl aryl, and halo substituents.

2. 4-(4-Pyridinyl)isatoic anhydride.

* * * * *

UNITED STATES PATENT AND TRADEMARK OFFICE
CERTIFICATE OF CORRECTION

PATENT NO. : 4,524,203
DATED : June 18, 1985
INVENTOR(S) : Thomas J. Walter et al.

It is certified that error appears in the above-identified patent and that said Letters Patent is hereby corrected as shown below:

Column 4, line 48, "phenoxy phenyl aryl, and" should read -- phenoxyphenyl, and --.

Signed and Sealed this

Eighth Day of October 1985

[SEAL]

Attest:

DONALD J. QUIGG

Attesting Officer

Commissioner of Patents and
Trademarks—Designate